United States Patent
Leconte et al.

(10) Patent No.: US 7,385,074 B2
(45) Date of Patent: Jun. 10, 2008

(54) METHOD FOR THE HEMIHYDROGENATION OF DINITRILES IN ORDER TO FORM AMINONITRILES

(75) Inventors: Philippe Leconte, Meyzieu (FR); Joseph Lopez, Villeurbanne (FR); Philippe Marion, Vernaison (FR)

(73) Assignee: Rhodia Polyamide Intermediates, Saint Fons (FR)

( * ) Notice: Subject to any disclaimer, the term of this patent is extended or adjusted under 35 U.S.C. 154(b) by 529 days.

(21) Appl. No.: 10/481,027

(22) PCT Filed: Jun. 13, 2002

(86) PCT No.: PCT/FR02/02019

§ 371 (c)(1), (2), (4) Date: May 27, 2004

(87) PCT Pub. No.: WO03/000650

PCT Pub. Date: Jan. 3, 2003

(65) Prior Publication Data

US 2004/0220423 A1  Nov. 4, 2004

(30) Foreign Application Priority Data

Jun. 22, 2001  (FR) .................. 01 08248

(51) Int. Cl.
*C07C 255/04* (2006.01)
(52) U.S. Cl. ..................... 558/459
(58) Field of Classification Search ................ 558/459
See application file for complete search history.

(56) References Cited

U.S. PATENT DOCUMENTS

| 5,527,946 A | 6/1996 | Melder et al. |
| 6,114,567 A | 9/2000 | Melder et al. |
| 6,156,694 A | 12/2000 | Harper |

FOREIGN PATENT DOCUMENTS

FR   2785608 A   5/2000

*Primary Examiner*—James O. Wilson
*Assistant Examiner*—Ebenezer Sackey
(74) *Attorney, Agent, or Firm*—Buchanan, Ingersoll & Rooney, PC

(57) ABSTRACT

The present invention relates to the hemihydrogenation of dinitriles to corresponding aminonitriles.

23 Claims, No Drawings

METHOD FOR THE HEMIHYDROGENATION OF DINITRILES IN ORDER TO FORM AMINONITRILES

The present invention relates to the hemihydrogenation of dinitriles to corresponding aminonitriles.

The hydrogenation of dinitriles is generally carried out in order to prepare the corresponding diamines; thus, particularly, the hydrogenation of adiponitrile results in hexamethylenediamine, itself being one of the two base compounds for the preparation of polyamide-6,6.

However, it can sometimes prove necessary to prepare not the diamine but the intermediate aminonitrile. This is the case, for example but not limitingly, in the hemihydrogenation of adiponitrile to aminocapronitrile, which is capable of subsequently being converted to caprolactam, the base compound for polyamide-6, or directly to polyamide-6.

Thus, patent U.S. Pat. No. 4,389,348 discloses a process for the hydrogenation of dinitrile to ω-aminonitrile by hydrogen in ammonia and aprotic solvent medium in the presence of rhodium deposited on a basic support.

Patent U.S. Pat. No. 5,151,543 discloses a process for the partial hydrogenation of dinitriles to aminonitriles in a solvent in molar excess of at least 2/1 with respect to the dinitrile, comprising liquid ammonia or an alkanol comprising an inorganic base which is soluble in the said alkanol, in the presence of a catalyst of Raney cobalt or nickel type.

Patent U.S. Pat. No. 5,981,790 relates to a process for the partial hydrogenation of dinitriles to aminonitriles in the presence of a catalyst based on Raney nickel or Raney cobalt in the presence of at least 0.5% by weight of water in the reaction medium comprising the products to be hydrogenated and the hydrogenated compounds. The catalyst is used in conjunction with a base.

These various processes make it possible to jointly produce an aminonitrile and a diamine in relatively different ratios and with relatively high production of by-products which are difficult to separate. Studies are continually being carried out to modify this ratio in order in particular to increase the production of aminonitrile at the expense of that of diamine and also to reduce the formation of by-products.

Thus, Patent Application WO 00/64862 discloses a process for the partial hydrogenation of a dinitrile for the production of aminonitriles in the presence of a hydrogenation catalyst, of a liquid ammonia solvent or of an alkanol and of a compound which makes it possible to improve the selectivity of the reaction for aminonitriles.

Provision has also been made for catalytic systems based on nickel doped with one or more other metal elements, such as titanium, copper and iron, in order to improve the activity of the catalyst or its selectivity for aminonitrile or to decrease the level of undesirable by-products. Such catalytic systems are disclosed in Patents FR 2 785 608 and U.S. Pat. No. 5,801,286.

One of the objects of the present invention is to provide a process for the preferential hydrogenation of a single nitrile functional group of a dinitrile (referred to in the present text as hemihydrogenation), so as to prepare predominantly the corresponding aminonitrile and only to a minor extent the diamine, with minimal formation of by-products.

More specifically, the invention relates to a process for the hemihydrogenation of aliphatic dinitriles to corresponding aminonitriles using hydrogen and a hydrogenation catalyst. This process is characterized in that the hydrogenation catalyst comprises nickel or Raney nickel and a doping element chosen from rhodium or iridium.

According to another characteristic of the invention, the catalyst of the invention can comprise one or more additional dopants chosen from Groups 3 to 12 of the Periodic Table of the Elements (according to the IUPAC nomenclature employed in: Handbook of Chemistry and Physics, 80th edition, 1999-2000). In particular, the groups comprising titanium, chromium, iron, zirconium, vanadium, manganese, bismuth, tantalum, ruthenium, platinum, palladium, niobium, hafnium, bismuth and the rare earth metal elements are preferred. The catalyst of the invention cannot comprise copper, silver and/or gold.

In a preferred embodiment of the invention, a strong inorganic base deriving from an alkali metal or an alkaline earth metal or ammonium is added to the hydrogenation medium. However, when the hydrogenation is carried out in the presence of liquid ammonia, the strong inorganic base is not necessarily needed.

According to another preferred characteristic of the invention, the starting hydrogenation medium comprises water in a proportion of at least 0.5% by weight with respect to all of the liquid compounds of the said medium, diamine and/or aminonitrile capable of being formed from the dinitrile to be hydrogenated, and unconverted dinitrile, in a proportion for the combination of these three compounds at 80% to 99.5%.

In another embodiment of the process of the invention, the reaction can be carried out in the presence of a solvent, such as an alcohol. In this case, the presence of water is not obligatory.

The hemihydrogenation reaction can be carried out in the presence of an additive which increases the selectivity for aminonitrile with respect to that obtained with the additive free system described above, while maintaining the overall selectivity for aminonitrile and diamine at a level at least substantially equivalent to that obtained without the additive. Such additives are disclosed in particular in Patent Application WO 00/64862.

According to the invention, the doping element rhodium or iridium is present in the catalyst, advantageously, according to an (Rh or Ir)/Ni ratio by weight of between 0.05% and 10% and preferably between 0.1% and 5%.

The amount of additional dopant other than rhodium or iridium which the catalyst can comprise generally represents from 0% to 5% by weight of the weight of the nickel.

The catalyst is prepared according to conventional methods for the preparation of metal catalysts.

Thus, by way of example, Raney nickels are catalysts widely used industrially for hydrogenation reactions. They are prepared by alkaline attack on aluminium-rich Al/Ni alloys comprising, if appropriate, other metals, generally referred to as dopants or promoters. The catalyst is composed of agglomerates of nickel crystallites with a high specific surface and with a variable concentration of residual aluminium. The dopant can be added at various stages in the preparation of the catalyst: during the preparation of the alloy by melting the various metals, during the activation of the alloy by alkaline attack in the presence of Rh or Ir salt, or after activation of the alloy (cf. Patents WO 95/17959 and WO 95/17960).

This catalyst generally comprises an aluminium content, expressed by weight with respect to the weight of the nickel, of less than or equal to 10%.

The catalyst of the invention can be employed in various forms, such as grains, granules or powder.

The process of the invention makes it possible to obtain, for a degree of conversion of the dinitrile of greater than 70%, a selectivity for aminonitrile of greater than 55% and an overall selectivity for aminonitrile and diamine of greater than 90%.

The aliphatic dinitriles which can be employed in the process of the invention are more particularly the dinitriles of general formula (I):

NC—R—CN     (I)

in which R represents a linear or branched alkylene or alkenylene group having from 1 to 12 carbon atoms.

Use is preferably made, in the process of the invention, of the dinitriles of formula (I) in which R represents a linear or branched alkylene radical having from 2 to 6 carbon atoms.

Mention may in particular be made, as examples of such dinitriles, of adiponitrile, methylglutaronitrile, ethylsuccinonitrile, malononitrile, succinonitrile, glutaronitrile and their mixtures, in particular the mixtures of adiponitrile and/or of methylglutaronitrile and/or of ethylsuccinonitrile which are capable of originating from the same process for the synthesis of adiponitrile.

In practice, the case where $R=(CH_2)_4$ will be the commonest, as this corresponds to the use of adiponitrile (and) in the present process.

The strong inorganic base is generally composed of alkali metal or alkaline earth metal or ammonium hydroxides, carbonates and alkoxides. It is preferably chosen from alkali metal or ammonium hydroxides, carbonates and alkoxides.

Preferably, the strong inorganic base employed is chosen from the following compounds: LiOH, NaOH, KOH, RbOH, CsOH, $NH_4OH$ and their mixtures.

In practice, NaOH and KOH are generally used, although RbOH and CsOH can give very good results.

The reaction medium has a composition which varies according to the type of implementation of the process.

Water is usually present in the reaction medium in an amount of less than or equal to 20% by weight. Preferably, the content of water in the reaction medium is between 2% and 15% by weight with respect to the combined liquid constituents of the said medium.

In addition to or as a substitute for the water, it is possible to provide at least one other solvent, generally of alcohol type. The alcohols which are more particularly suitable are, for example, methanol, ethanol, propanol, isopropanol, butanol and the mixtures of the said compounds.

Where it is employed with water, the alcoholic solvent represents from two to four parts by weight per one part by weight of water and preferably three parts per one part of water.

According to another preferred characteristic of the invention, the starting hydrogenation medium comprises diamine which is coproduced by the hydrogenation. It is, for example, hexamethylenediamine when the dinitrile substrate is adiponitrile.

The mean concentration under continuous conditions of the aminonitrile and/or of the diamine in the reaction medium is advantageously between 35% and 99% by weight with respect to the weight of the combined solvent included in the said reaction medium and more preferably between 45% and 89% as weight by weight.

The overall concentration of targeted aminonitrile and/or of the corresponding diamine and of the unconverted dinitrile in the reaction medium is generally between 85% and 99% by weight with respect to the combination of the liquids included in the said reaction medium.

The reaction medium can comprise liquid or dissolved ammonia. Generally, the ammonia represents from 0% to 50% by weight of the reaction medium and preferably from 0% to 15%.

The amount of alkali metal or alkaline earth metal or ammonium hydroxide in the reaction medium varies according to the nature of the said reaction medium.

When the reaction medium comprises only water, the reaction products and optionally ammonia or the diamine, as liquid solvent medium, the amount of alkali metal or alkaline earth metal hydroxide is advantageously greater than or equal to 0.1 mol/kg of catalyst, preferably between 0.1 mol and 2 mol/kg of catalyst and more preferably still between 0.2 and 1.0 mol/kg of catalyst.

The amount of catalyst employed can vary very widely according in particular to the method of operation adopted or the reaction conditions chosen. Thus, if the dinitrile is introduced gradually into the reaction medium, the catalyst/dinitrile to be hydrogenated ratio by weight will be much higher than if all the dinitrile is employed from the beginning of the reaction. By way of indication, use may be made of 0.5% to 50% by weight of catalyst with respect to the total weight of the reaction medium and generally of 1% to 35%.

According to a preferred embodiment of the invention, the catalyst is preconditioned before it is introduced into the hemihydrogenation medium. This preconditioning is advantageously carried out according to the process disclosed in the unpublished French Patent Application No. 00.02997. This process consists briefly in mixing the hydrogenation catalyst with a predetermined amount of strong inorganic base and a solvent in which the strong inorganic base is not very soluble. According to the invention, the medium comprising the catalyst thus conditioned is fed to the hydrogenation reactor, the hydrogenation reaction being carried out according to the usual conditions and procedures already disclosed in the literature.

The selectivity for aminonitrile, at a constant degree of conversion of the dinitrile, depends in particular on the nature and on the content of dopant, on the amount of water in the reaction medium, on the nature of the base and on the base/Ni ratio.

The process of the invention is generally carried out at a reaction temperature of less than or equal to 150° C., preferably of less than or equal to 120° C. and more preferably still of less than or equal to 100° C.

In practical terms, this temperature is between ambient temperature (approximately 20° C.) and 100° C.

Prior to, simultaneously with or subsequent to the heating, the reaction chamber is brought to the appropriate hydrogen pressure, that is to say, in practice, between 1 bar (0.10 MPa) and 100 bar (10 MPa) and preferably between 5 bar (0.5 MPa) and 50 bar (5 MPa).

The duration of the reaction can vary as a function of the reaction conditions and of the catalyst.

In a batchwise method of operation, it can vary from a few minutes to several hours.

It should be noted that a person skilled in the art can vary the order of occurrence of the stages of the process according to the invention, according to the operating conditions.

The other conditions which govern the hydrogenation (continuous or batchwise) in accordance with the invention relate to conventional technical arrangements known per se.

The invention is illustrated by the examples which follow of the hemihydrogenation of adiponitrile to 6-aminocapronitrile In these examples, the following abbreviations may be used:
AdN=adiponitrile
ACN=aminocapronitrile
HMD=hexamethylenediamine
DC=degree of conversion
CY=selectivity with respect to the converted starting substrate (in this instance with respect to the AdN).

COMPARATIVE EXAMPLE

The following are charged to a 100 ml stainless steel reactor equipped with a stirrer of self-suction Rushton type, with means for introducing the reactants and hydrogen and with a temperature regulation system:

| hexamethylenediamine | 24 g |
| water | 5.3 g |
| KOH | 0.33 mmol |
| Raney Ni (comprising 1.7% of Cr) | 0.65 g |

In this example, there is 0.5 mol KOH/kg Ni.

After having purged the reactor with nitrogen and then with hydrogen, the pressure is adjusted to 2 MPa of hydrogen and the reaction mixture is heated to 50° C.

24 g of adiponitrile are subsequently introduced instantaneously via a dropping funnel pressurized to 2.5 MPa by a pressure reducer placed on a hydrogen supply at 5 MPa. The time is taken as equal to 0 at this point. The progress of the reaction is monitored by the consumption of hydrogen in the hydrogen supply, the pressure in the reactor being kept constant at 2.5 MPa, and by the analysis by gas chromatography (GC) of a withdrawn sample of the reaction mixture. When the maximum aminocapronitrile yield is reached, the reaction is halted by halting the stirring, cooling the reaction mixture and then depressurizing.

The following results are obtained:

| duration of the reaction | 33 min |
| DC of the AdN: | 79.6% |
| CY for ACN: | 70.1% |
| CY for HMD | 29.5% |
| CY for other products: | 0.4% |

Example 1

Ni Doped With Rh

The following are charged to a 100 ml stainless steel reactor equipped with a stirrer of self-suction Rushton type, with means for introducing the reactants and hydrogen and with a temperature regulation system:

| hexamethylenediamine | 24 g |
| water | 5.3 g |
| KOH | 0.66 mmol |
| Raney Ni doped with 2.7% of Rh | 1.3 g |

In this example, there is 0.5 mol KOH/kg Ni.

After having purged the reactor with nitrogen and then with hydrogen, the pressure is adjusted to 2 MPa of hydrogen and the reaction mixture is heated to 50° C.

24 g of adiponitrile are subsequently introduced instantaneously via a dropping funnel pressurized to 2.5 MPa by a pressure reducer placed on a hydrogen supply at 5 MPa. The time is taken as equal to 0 at this point. The progress of the reaction is monitored by the consumption of hydrogen in the supply, the pressure in the reactor being kept constant at 2.5 MPa, and by the analysis by gas chromatography (GC) of a withdrawn sample of the reaction mixture. When the optimum aminocapronitrile yield is reached, the reaction is halted by halting the stirring, cooling the reaction mixture and then depressurizing.

The following results are obtained:

| duration of the reaction | 66 min |
| DC of the AdN: | 83.3% |
| CY for ACN: | 71.7% |
| CY for HMD | 28% |
| CY for other products: | 0.3% |

Example 2

Ni Doped With Ir

The following are charged to a 100 ml stainless steel reactor equipped with a stirrer of self-suction Rushton type, with means for introducing the reactants and hydrogen and with a temperature regulation system:

| hexamethylenediamine | 24 g |
| water | 5.3 g |
| KOH | 0.13 mmol |
| Raney Ni doped with 2.8% of Ir | 1.3 g |

In this example, there is 0.2 mol KOH/kg Ni.

After having purged the reactor with nitrogen and then with hydrogen, the pressure is adjusted to 2 MPa of hydrogen and the reaction mixture is heated to 50° C.

24 g of adiponitrile are subsequently introduced instantaneously via a dropping funnel pressurized to 2.5 MPa by a pressure reducer placed on a hydrogen supply at 5 MPa. The time is taken as equal to 0 at this point. The progress of the reaction is monitored by the consumption of hydrogen in the supply, the pressure in the reactor being kept constant at 2.5 MPa, and by the analysis by gas chromatography (GC) of a withdrawn sample of the reaction mixture. When the optimum aminocapronitrile yield is reached, the reaction is halted by halting the stirring, cooling the reaction mixture and then depressurizing.

The following results are obtained:

| duration of the reaction | 72 min |
| DC of the AdN: | 81.2% |
| CY for ACN: | 73.8% |
| CY for HMD | 25.4% |
| CY for other products: | 0.8% |

The invention claimed is:
1. Process for the hemihydrogenation of a dinitrile to corresponding aminonitrile in a liquid medium, wherein the process is carried out in the presence of a nickel or Raney nickel catalyst comprising a doping element selected from rhodium or iridium.

2. Process according to claim 1, wherein the (Rh or Ir)/Ni ratio by weight of the catalyst used is between 0.05% and 10%.

3. Process according to claim 2, wherein the abovementioned ratio by weight is between 0.1% and 5%

4. Process according to claim 1, wherein the catalyst comprises one or more additional dopants selected from titanium, chromium, iron, zirconium, vanadium, manganese, bismuth, tantalum, ruthenium, platinum, palladium, niobium, hafnium or the rare earth metal elements, with the exception of copper, silver or gold.

5. Process according to claim 4, wherein the amount of additional dopant other than rhodium or iridium which the catalyst comprises represents from 0% to 5% by weight of the weight of the nickel.

6. Process according to claim 1, which is carried out in the presence of a strong inorganic base.

7. Process according to claim 1, wherein said dinitrile comprises dinitrile substrates of formula (I):

tNC—R—CN  (I)

in which R represents a linear or branched alkylene group having from 1 to 12 carbon atoms.

8. Process according to claim 1, Wherein the mean concentration dinitrile in the reaction medium lies between 10% and 45% as weight by weight, when the process is carried out continuously.

9. Process according to claim 1, which is carried out in the presence of LiOH, NaOH, KOH, RhOH, CsOH or NH$_4$OH or of their mixtures.

10. Process according to claim 1, wherein the starting liquid reaction medium comprises water representing an amount of 1% to 20% by weight with respect to the weight of the total reaction medium.

11. Process according to claim 10, wherein the concentration of water is between 1 and 15% as weight by weight of the reaction medium.

12. Process according to claim 1, wherein the reaction medium comprises a solvent of alcohol type.

13. Process according to claim 12, wherein the alcohol is selected from methanol, ethanol, propanol, isopropanol, butanol or mixtures of said compounds.

14. Process according to claim 1, wherein the reaction medium comprises diamine which is coproduced by the hydrogenation.

15. Process according to claim 14, wherein the mean concentration under continuous conditions of the aminonitrile and/or of the diamine in the reaction medium is between 35% and 99% by weight with respect to the weight of the combined solvent included in said reaction medium.

16. Process according to claim 15, wherein the mean concentration of the aminonitrile and/or of the diamine is between 45% and 89% as weight by weight of the combined solvent in the reaction medium.

17. Process according to claim 1, wherein the reaction medium comprises liquid or dissolved ammonia.

18. Process according to claim 17, wherein the ammonia represents from 0% to 50% by weight of the reaction medium.

19. Process according to claim 6, wherein the amount of alkali metal or alkaline earth metal hydroxide or ammonia is greater than or equal to 0.1 mol/kg of catalyst.

20. Process according to claim 19, wherein said amount of hydroxide is between 0.1 and 2 mol/kg of catalyst.

21. Process according to claim 19, wherein said amount of hydroxide is between 0.2 and 1.0 mol/kg of catalyst.

22. Process according to claim 1, which is carried out at a temperature of less than or equal to 150° C.

23. Process according to claim 1, which is carried out under a hydrogen pressure of between 0.10 and 10 MPa.

* * * * *